United States Patent [19]

Kitano et al.

[11] Patent Number: 4,880,562
[45] Date of Patent: Nov. 14, 1989

[54] LIQUID CRYSTAL COMPOUND

[75] Inventors: Kisei Kitano; Manabu Uchida; Makoto Ushioda; Toshiharu Suzuki, all of Kanagawa, Japan

[73] Assignee: Chisso Corporation, Ohsaka, Japan

[21] Appl. No.: 312,053

[22] Filed: Feb. 17, 1989

[30] Foreign Application Priority Data

Feb. 26, 1988 [JP] Japan .................................. 63-43385

[51] Int. Cl.$^4$ ......................... G02F 1/13; C09K 19/30; C07C 121/70
[52] U.S. Cl. ............................ 252/299.63; 252/299.5; 350/350 R; 558/425
[58] Field of Search ........................ 252/299.5, 299.63; 350/250 R; 558/425

[56] References Cited

U.S. PATENT DOCUMENTS

| | | | |
|---|---|---|---|
| 4,528,114 | 7/1985 | Petrzilka et al. | 252/299.63 |
| 4,565,425 | 1/1986 | Petrzilka et al. | 252/299.5 |
| 4,621,901 | 11/1986 | Petrzilka et al. | 252/299.63 |
| 4,676,604 | 6/1987 | Petrzilka | 252/299.63 |
| 4,770,503 | 9/1988 | Buchecker et al. | 252/299.63 |

FOREIGN PATENT DOCUMENTS 168683 1/1986 European Pat. Off. ........ 252/299.63
61-27931 2/1986 Japan ................................ 252/299.63

OTHER PUBLICATIONS

Buchecker R., et al., Mol. Cryst. Liq. Cryst., vol. 149, pp. 359–373 (1987).
Petrzikla M., Mol. Cryst. Liq. Cryst., vol. 131, pp. 109–123 (1985).
Schadt M. et al., Mol. Cryst. Liq. Cryst., vol. 122, No. 1–4, pp. 241–261 (1985).

Primary Examiner—Teddy S. Gron
Attorney, Agent, or Firm—Wenderoth, Lind & Ponack

[57] ABSTRACT

A liquid crystalline compound useful as a component of liquid crystal compositions for TN mode display elements and having a large positive $\Delta\epsilon$ value and also a low viscosity for the $\Delta\epsilon$ value and a liquid crystal composition containing the compound are provided, which compound is expressed by the formula

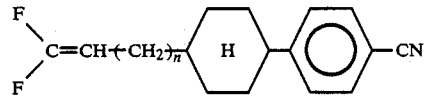

wherein n represents an integer of 0 to 20.

4 Claims, No Drawings

LIQUID CRYSTAL COMPOUND

BACKGROUND OF THE INVENTION

1. Field of the Invention

This invention relates to a novel liquid crystalline compound useful for display elements and a liquid crystal composition containing the same.

2. Description of the Related Art

Liquid crystal substances and their compositions have been used for various display devices utilizing the dielectric anisotropy (hereinafter abbreviated to $\Delta\epsilon$) and optical anisotropy (hereinafter abbreviated to $\Delta n$) in the liquid crystal phases thereof.

Liquid crystal display modes include various ones corresponding to the electrooptical effects to which the modes are applied, such as those of electric field control birefringence type (ECB type), twisted nematic type (TN type), super twist birefringence type (SBE type), dynamic scattering type (DS type), Guest-host type, etc. Liquid crystal materials used for display devices should be together provided with various specific features such as a broad mesomorphic range, a low viscosity, a large positive $\Delta\epsilon$ value or negative $\Delta\epsilon$ value and no large change in various specific features of display elements (particularly threshold voltage) over a broad temperature range, etc., depending on the respective display modes and also depending on various specific features required for display elements.

At present, however, there is no single compound which is practically usable in the aspects of mesomorphic range, operating voltage and response properties. Thus, mixtures of several kinds of liquid crystal compounds or mixtures of several kinds of liquid crystal compounds with compounds latently having liquid crystalline properties or non-liquid crystal substances have been practically used.

SUMMARY OF THE INVENTION

The object of the present invention is to provide a liquid crystalline compound useful as a component of lqiuid crystal compositions used for TN mode liquid crystal display elements and particularly a liquid crystalline compound having a large positive $\Delta\epsilon$ value and also a low viscosity for the $\Delta\epsilon$ value. A liquid crystalline compound referred to herein means not only compounds exhibiting liquid crystal phases, but also compounds which exhibit no liquid crystal phase by themselves, but when dissolved in other liquid crystal compounds, effectively function in a certain aspect of liquid crystal behavior.

The present invention resides in a compound expressed by the formula

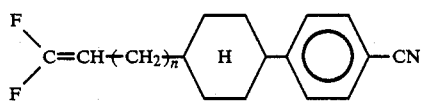
(I)

wherein n represents 0 and a natural number of 1 to 20, and a liquid crystal mixture containing at least one member of the compound.

DETAILED DESCRIPTION OF PREFERRED EMBODIMENTS

The compounds of the formula (I) of the present invention will be concretely illustrated below:

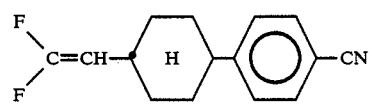
(1)

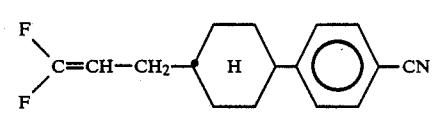
(2)

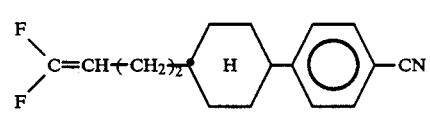
(3)

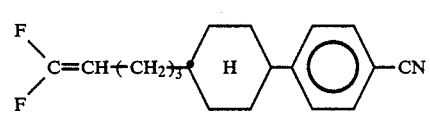
(4)

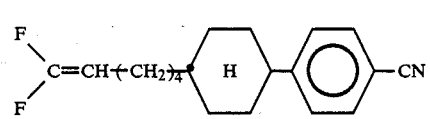
(5)

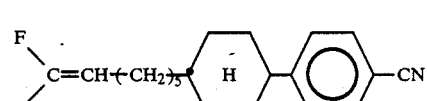
(6)

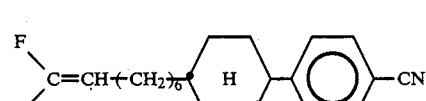
(7)

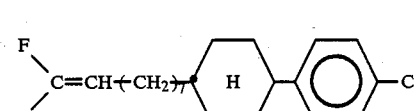
(8)

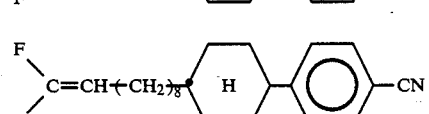
(9)

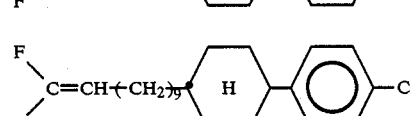
(10)

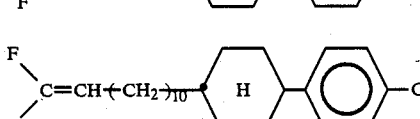
(11)

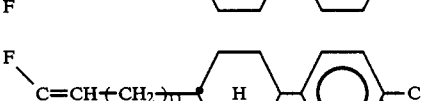
(12)

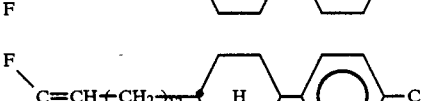
(13)

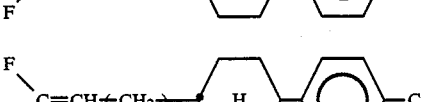
(14)

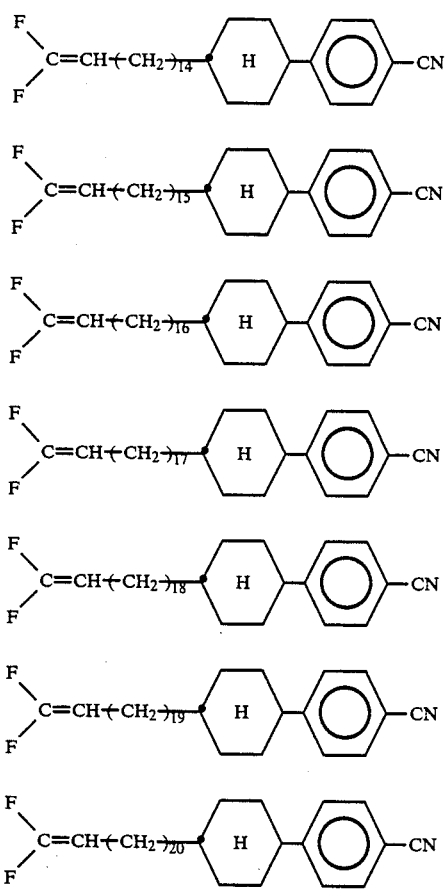

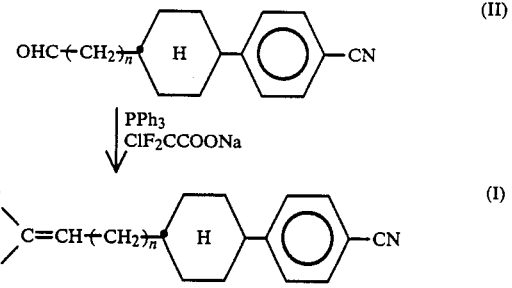

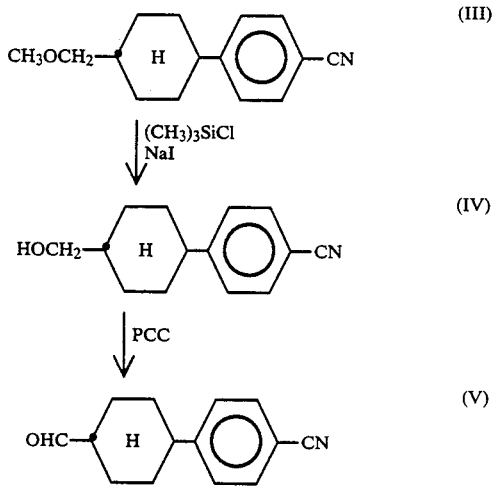

wherein n is as defined above.

Namely the compound is obtained by reacting an aldehyde derivative (II) corresponding to the objective product obtained as described later, with triphenylphosphine and sodium chlorodifluoroacetate in a solvent such as diethylene glycol dimethyl ether, dimethylformamide, N-methylpyrrolidone or the like. This reaction is known as Wittig's reaction i.e. a reaction of forming carbon-carbon double bond (e.g. see Org. Synth. Coll. Vol. V, 390 (1973)). By subjecting the reaction product to conventional separation and purification operations, that is, vacuum distillation, chromatography, recrystallization, etc., it is possible to obtain the objective compound (I). The aldehyde derivative (II) used as a raw material can be prepared for example according to the following preparation:

The compound of the formula (I) of the present invention includes some compounds which are monotropic but have nematic properties in the vicinity of temperatures at which liquid crystal display devices are used. Further, the compound of the present invention has a relatively low viscosity and is suitable for preparing liquid crystal display devices having a higher response rate. Still further, the compound of the present invention has a relatively large positive dielectric anisotropy value and is suitable for preparing liquid crystal compositions from which liquid crystal display devices having a low driving voltage can be obtained.

The compound of the present invention has a stability to heat, light, electricity, air, moisture, etc. required for liquid crystal dispaly materials and also has a superior compatibility with other existing liquid crystalline materials for example liquid crystal compounds of esters, Schiff's base compounds, ethane compounds, acetylene compounds, azoxy compounds, biphenyl compounds, cyclohexane compounds, pyrimidine compounds, pyridine compounds, etc.; hence when the compound is mixed with these compounds, it is possible to prepare liquid crystal materials suitable to various use applications.

The compound of the present invention can be prepared for example according to the following preparation:

Namely, known trans-4-methoxymethyl-1-(4-cyanophenyl)cyclohexane (III) (e.g. obtained according to a process disclosed in Japanese patent application laid-open No. Sho 58-59956/1983) is reacted with trimethylsilyl chloride and sodium iodide in acetonitrile as solvent according to a known process e.g. disclosed in J. Org. Chem., 44, 1247 (1979) to obtain trans-4-(4-cyanophenyl)cyclohexylcarbinol (IV), followed by oxidizing this compound (IV) with pyridinium chlorochromate (PCC) into an aldehyde according to the process disclosed in Synthesis, 245 (1982) to obtain trans-4-(4-cyanophenyl)cyclohexylcarboaldehyde (V). This compound (V) corresponds to a compound of the aldehyde derivative (II) wherein n=0. Further, compounds of the aldehyde derivative (II) wherein n=1 to 20 may be prepared according to the following preparation:

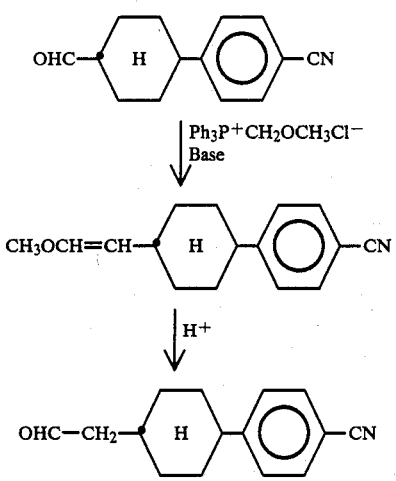

Namely, an aldehyde derivative (V) is reacted with methoxymethyltriphenylphosphonium chloride and a base such as potassium t-butoxide, sodium methylate, phenyllithium, n-butyllithium or the like according to Wittig's reaction to obtain a methoxyvinyl derivative (VI), followed by heating this compound (VI) under an acidic condition (for example, heating with hydrochloric acid in tetrahydrofuran as solvent) to obtain an aldehyde derivative (VII) having one more methylene increased relative to the original aldehyde (V). When the aldehyde derivative (V) is subjected to the Wittig's reaction and the acid treatment reaction successively n times, it is possible to obtain the aldehyde derivative (II) wherein n=1 or more.

The present invention will be described in more detail by way of Examples, but it should not be construed to be limited thereto. In Examples, the Crystal⟷Nematic phase transition point and the nematic phase⟷isotropic liquid phase transition point are abbreviated to CN point and NI point, respectively.

EXAMPLE 1

Preparation of trans-1-(2,2-difluoro-1-ethenyl)-4-(4-cyanophenyl)cyclohexane (a compound of the formula (I) wherein n=0, i.e. compound (1))

(i) Preparation of trans-4-(4-cyanophenyl)cyclohexanecarboaldehyde

Trimethylsilyl chloride (305.6 g, 2.81 mols) was dropwise added to trans-4-methoxymethyl-1-(4-cyanophenyl)-cyclohexane (III) (322.5 g, 1.41 mol), NaI (421.6 g, 2.81 mols) and acetonitrile (2.5 l) in nitrogen atmosphere with stirring at 35° C. over 30 minutes, followed by agitating the mixture for 20 minutes, cooling down to 10° C., filtering the reaction mixture by suction, pouring the mother liquor in ice water (2 Kg), extracting with chloroform (1.5 l), subjecting the resulting chloroform solution to twice washing with a 10% by weight aqueous solution of thiosulfate (0.5 l) and separating, further three times subjecting to washing with water (1 l) and separating, distilling off chloroform and three times recrystallizing the residue from toluene (300 ml) to obtain trans-4-(4-cyanophenyl)-cyclohexylcarbinol (IV) (182.5 g, 0.848 mol) having a m.p. of 108.5°–110.8° C. On the other hand, pyridinium chlorochromate (161.7 g, 0.750 mol) was added to dichloromethane (1 l), followed by instantaneously adding to the solution a solution of trans-4-(4-cyanophenyl)cyclohexylcarbinol (IV) (107.6 g, 0.500 mol) obtained above (107.6 g, 0.500 mol) in dichloromethane (0.7 l) with stirring at room temperature, further agitating the mixture at room temperature for 1.5 hour, adding diethyl ether (1 l) to the resulting reaction solution and concentrating the supernatant according to florysil column chromatography to obtain trans-4-(4-cyanophenyl)cyclohexylcarboaldehyde (V) (101.2 g, 0.474 mol).

(ii) Preparation of the captioned compound

Trans-4-(4-cyanophenyl)cyclohexylcarboaldehyde (V) (47.8 g, 0.224 mol) obtained in item (i), triphenylphosphine (64.6 g, 0.246 mol), sodium chlorodifluoroacetate (54.6 g, 0.538 mol) and dimethylformamide (200 ml) were heated with stirring in nitrogen atmosphere at about 90° C. for 3 hours, followed by cooling the resulting solution down to room temperature, adding thereto toluene (200 ml) and water (200 ml), subjecting the resulting toluene solution to three times washing with water (200 ml) and separating, drying with anhydrous sodium sulfate, separating the drying agent, distilling the resulting residue under reduced pressure (b.p.: 136°–138° C./1 mmHg), dissolving the distillate in toluene, purifying according to silica gel chromatography, repeating recrystallization from methanol and drying to obtain the objective captioned compound (20.3 g, 0.0821 mol). This compound had a m.p. of 59.3° C. and an NI point of 9.8° C. (monotropic).

EXAMPLE 2

Preparation of trans-1-(3,3-difluoro-2-propenyl)-4-(4-cyanophenyl)cyclohexane (a compound of the formula (I) wherein n=1, i.e. compound (2))

(i) Preparation of trans-4-(4-cyanophenyl)cyclohexylacetaldehyde (VII)

Commercially available methoxymethyltriphenylphosphonium chloride (127.5 g, 0.372 mol) was added to methyl t-butyl ether (1 l), followed by adding potassium t-butoxide (43.1 g, 0.384 mol) in argon atmosphere with stirring at −10° C. over 10 minutes, agitating the reaction solution at 0° C. for one hour, dropwise adding a solution of trans-4-(4-cyanophenyl)cyclohexylcarboaldehyde (V) obtained in Example 1, (i) (44.1 g, 0.207 mol) in methyl t-butyl ether (200 ml) at =10° C. over 15 minutes, agitating the resulting reaction solution at 0° C. for one hour, adding toluene (0.3 l) and water (0.3 l), subjecting the resulting toluene solution to four times washing with water (0.3 l) and separating, drying with anhydrous sodium sulfate, separating the drying agent, distilling off toluene, dissolving the resulting residue in ethyl acetate (100 ml) on heating, allowing the solution to stand still for one day, filtering off deposited crystals, concentrating the mother liquor, dissolving the concentrate in heptane, purifying according to silica gel column chromatography to obtain trans-1-(2-methoxy-1-ethenyl)-4-(cyanophenyl)cyclohexane (39.8 g, 0.165 mol), adding to the total quantity, tetrahydrofuran (500 ml) and 2N-hydrochloric acid (120 ml), heating the mixture under reflux with stirring for one hour, cooling the resulting reaction solution, adding toluene (300 ml) and water (1 l), washing subjecting the resulting toluene solution to three times washing with water (1 l) and separating, drying with anhydrous sodium sulfate, separating the drying agent and distilling off toluene to obtain trans-4-(4-cyanophenyl)cyclohexylacetaldehyde (VII) (35.4 g, 0.156 mol).

(ii) Preparation of the captioned compound

Trans-4-(4-cyanophenyl)cyclohexylacetaldehyde (VII) obtained in item (i) (35.4 g, 0.156 mol), triphenylphosphine (49.0 g, 0.187 mol), sodium chlorodifluoroacetate (47.5 g, 0.311 mol) and dimethylformamide (100 ml) were heated with stirring in nitrogen gas current at about 90° C. for 3 hours, followed by cooling the resulting solution down to room temperature, adding toluene (200 ml) and water (200 ml) to the solution, subjecting the resulting toluene solution to three times washing with water (200 ml) and separating, drying with anhydrous sodium sulfate, separating the drying agent, distilling off toluene, distilling the resulting residue under reduced pressure (b.p.: 156°–158° C./0.5 mmHg), dissolving the distillate in toluene, purifying the solution according to silica gel chromatography, repeating crystallization from ethanol and drying to obtain the objective captioned compound (18.6 g, 0.0712 mol). This compound had a m.p. of 30.8°–31.5° C. and an NI point of −37.3° C. according to extrapolation method.

EXAMPLE 3

Preparation of
trans-1-(4,4-difluoro-3-butenyl)-4-(4-cyanophenyl)cyclohexane (a compound of the formula (I) wherein n=2, i.e. compound (3))

(i) Preparation of trans-4-(4-cyanophenyl)cyclohexylpropylaldehyde

Commercially available methoxymethyltriphenylphosphornium chloride (15.7 g, 0.0458 mol) was added to tetrahydrofuran (100 ml), followed by dropwise adding a toluene solution (23 ml) of 25% by weight of phenyllithium in argon atmosphere with stirring at −10° C. over 10 minutes, agitating the reaction solution at 0° C. for 30 minutes, dropwise adding a solution of trans-4-(4-cyanophenyl)cyclohexylacetaldehyde (VII) obtained in Example 2(i) (7.3 g, 0.032 mol) in tetrahydrofuran (90 ml) at −10° C. over 10 minutes, agitating the reaction solution at 0° C. for 2 hours, adding toluene (100 ml) and water (200 ml), washing, subjecting the resulting toluene solution to three times washing with water (200 ml) and separating, drying with anhydrous sodium sulfate, separating the drying agent, distilling off toluene, dissolving the resulting residue in ethyl acetate (20 ml) on heating, allowing the solution to stand still at room temperature for one day, filtering off deposited crystals, concentrating the resulting mother liquor, dissolving the concentrate in heptane and purifying according to silica gel chromatography to obtain trans-1-(3-methoxy-2-propenyl)-4-(4-cyanophenyl)cyclohexane (4.4 g, 0.017 mol), adding to the total quantity thereof, tetrahydrofuran (70 ml) and 2N-hydrochloric acid (18 ml), heating the mixture under reflux with stirring for one hour, cooling the reaction solution, adding diethyl ether (50 ml) and water (50 ml) to the solution, subjecting the resulting diethyl ether to three times washing with water (50 ml) and separating, drying with anhydrous sodium sulfate, separating the drying agent and distilling off diethyl ether to obtain trans-4-(4-cyanophenyl)cyclohexylpropylaldehyde (4.2 g, 0.017 mol).

(ii) Preparation of the captioned compound

Trans-4-(4-cyanophenyl)cyclohexylpropylaldehyde obtained in item (i) (4.2 g, 0.017 mol), triphenylphosphine (5.2 g, 0.020 mol) sodium chlorodifluoroacetate (4.5 g, 0.029 mol) and dimethylformamide (30 ml) were heated in nitrogen gas current with stirring at about 90° C. for 3 hours, followed by cooling the reaction solution down to room temperature, adding diethyl ether (50 ml) and water (100 ml) to the solution, subjecting the resulting diethyl ether solution to three times washing with water (100 ml) and separating, drying with anhydrous sodium sulfate, separating the drying agent, distilling off diethyl ether, dissolving the residue in hexane, purifying according to silica gel column chromatography and repeating recrystallization from ethanol to obtain the objective captioned compound (1.6 g, 0.0058 mol). This compound exhibited a CN point of 11.6° C. and an NI point of 27.9° C.

EXAMPLE 4

Preparation of
trans-1-(5,5-difluoro-4-pentenyl)-4-(4-cyanophenyl)cyclohexane (a compound of the formula (I) wherein n=3, i.e. compound (4))

(i) Preparation of trans-4-(4-cyanophenyl)cyclohexylbutyraldehyde

Commercially available methoxymethyltriphenylphosphonium chloride (257 g, 0.75 mol) was added to tetrahydrofuran (500 ml), followed by adding potassium t-butoxide (84.2 g, 0.75 mol) in argon atmosphere with stirring at −10° C. over 40 minutes, agitating the reaction solution at 0° C. for one hour, dropwise adding a solution of trans-4-(4-cyanophenyl)cyclohexylpropylaldehyde obtained in the process of Example 3(i) (121 g, 0.50 mol) in tetrahydrofuran (400 ml) at −10° C. over one hour, agitating the reaction solution at 0° C. for one hour, further agitating it at 20° C. for 2 hours, adding toluene (1 l) and water (1 l) to the reaction solution at 0° C., subjecting the resulting toluene solution to four times washing with water (1 l) and separating, drying with anhydrous magnesium sulfate, separating the drying agent, distilling off toluene and purifying the resulting residue according to silica gel chromatography using heptane as an eluent to obtain trans-1-(4-methoxy-3-butenyl)-4-(4-cyanophenyl)cyclohexane (110.8 g, 0.41 mol), adding to the total quantity thereof tetrahydrofuran (1.5 l) and 2N-hydrochloric acid (0.4 l), heating the mixture under reflux with stirring for one hour, cooling the resulting reaction solution, adding diethyl ether (0.5 l) and water (1 l) to the solution, subjecting the resulting diethyl ether solution to three times washing with water (0.5 l) and separating, drying with anhydrous magnesium sulfate, separating the drying agent, concentrating the resulting material under reduced pressure to obtain a residue (120 g), recrystalling it from a mixed solvent of heptane and ethyl acetate (3:1) and drying to obtain trans-4-(4-cyanophenyl)cyclohexylbutyraldehyde (93.0 g, 0.36 mol).

(ii) Preparation of the captioned compound

Trans-4-(4-cyanophenyl)cyclohexylbutyraldehyde obtained in item (i) (20.0 g, 0.0783 mol), triphenylphosphine (24.7 g, 0.0940 mol), sodium chlorodifluoroacetate (23.9 g, 0.157 mol) and dimethylformamide (70 ml) were heated in nitrogen gas current with stirring at about 90° C. for 3 hours, followed by cooling the resulting reaction solution down to room temperature, adding toluene (200 ml) and water (200 ml) to the solution, subjecting the resulting toluene solution to three times washing with water (300 ml) and separating, drying with anhydrous sodium sulfate, separating the drying agent, distilling off toluene, purifying according to silica gel chromatography using heptane as an eluent, distilling off heptane, distilling the resulting residue under reduced pressure (b.p.: 164° C./0.5 mmHg), repeatedly recrystallizing the distillate from ethanol and drying to obtain the objective captioned compound (7.2 g, 0.0025 mol). This compound had a m.p. of 9.1° C. and an N-I point of −19.0° C. (monotropic).

EXAMPLE 5

Preparation of trans-1-(6,6-difluoro-5-hexenyl)-4-(4-cyanophenyl)cyclohexane (a compound of the formula (I) wherein n=4, i.e. compound (5))

(i) Preparation of trans-4-(4-cyanophenyl)cyclohexylpentylaldehyde

Commercially available methoxymethyltriphenylphosphonium chloride (120.8 g, 0.35 mol) was added to tetrahydrofuran (400 ml), followed by adding potassium t-butoxide (39.5 g, 0.35 mol) in argon atmosphere with stirring at −10° C. over 20 minutes, agitating the resulting reaction solution at 0° C. for one hour, dropwise adding a solution of trans-4-(4-cyanophenyl)cyclohexylbutylaldehyde obtained according to the process of Example 4(i) (60.0 g, 0.23 mol) in tetrahydrofuran (300 ml) at −10° C. over one hour, agitating the resulting reaction solution at 0° C. for one hour, further agitating at 20° C. for 2 hours, adding toluene (1 l) and water (1 l) to the resulting reaction solution at 0° C., subjecting the resulting toluene solution to four times washing with water (1 l) and separating, drying with anhydrous magnesium sulfate, separating the drying agent, distilling off toluene and purifying the resulting residue according to silica gel chromatography using heptane as an eluent to obtain trans-1-(5-methoxy-4-pentenyl)-4-(4-cyanophenyl)cyclohexane (52.6 g, 0.19 mol), adding to the total quantity thereof tetrahydrofuran (750 ml) and 2N-hydrochloric acid (190 ml), heating the mixture under reflux with stirring for one hour, cooling the resulting reaction solution, adding diethyl ether (0.5 l) and water (1 l) to the solution, subjecting the resulting diethyl ether solution to three times washing with water 0.5 l) and separating, drying with anhydrous magnesium sulfate, separating the drying agent, concentrating under reduced pressure to obtain a residue (50 g), recrystallizing it from a mixed solvent of heptane and ethyl acetate (3:1) and drying to obtain trans-4-(4-cyanophenyl)cyclohexylpentylaldehyde (43.1 g, 0.16 mol).

(ii) Preparation of the captioned compound

Trans-4-(4-cyanophenyl)cyclohexylpentylaldehyde obtained in item (i) (20.0 g, 0.074 mol), triphenylphosphine (23.5 g, 0.090 mol), sodium chlorodifluoroacetate (22.7 g, 0.149 mol) and dimethylformamide (70 ml) were heated in nitrogen gas current with stirring at about 90° C. for 3 hours, followed by cooling the reaction solution down to room temperature, adding toluene (200 ml) and water (200 ml) to the solution, subjecting the resulting toluene solution to three times washing with water (200 ml) and separating, drying with anhydrous sodium sulfate, separating the drying agent, distilling off toluene, purifying according to silica gel column chromatography using heptane as an eluent, distilling heptane, repeatedly recrystallizing the resulting residue from ethanol and drying to obtain the objective captioned compound (15.4 g, 0.051 mol). This compound exhibited a CN point of 19.6° C. and an NI point of 34.7° C.

EXAMPLE 6

(Use Example 1)

A liquid crystal composition A consisting of

| | |
|---|---|
| $C_3H_7$—(H)—(O)—CN | 24 wt. parts |
| $C_5H_{11}$—(H)—(O)—CN | 36 wt. parts |
| $C_7H_{15}$—(H)—(O)—CN | 25 wt. parts |
| $C_5H_{11}$—(H)—(O)—(O)—CN | 15 wt. parts | has an NI point of 72.0° C., a viscosity $\eta_{20}$ at 20° C. of 27.5 cp and a Δε of 11.0 ($\epsilon_\parallel$ =15.7, $\epsilon_{195}$ =4.7). This composition was filled in a TN cell of 9 μm thick. The resulting liquid crystal composition exhibited a threshold voltage of 1.83 V and a saturation voltage of 2.79 V. When trans-2-(2,2-difluoro-1-ethenyl)-4-(4-cyanophenyl)cyclohexane obtained in Example 1 (15 parts by weight) was added to the liquid crystal composition A (85 parts by weight), the resulting liquid crystal composition exhibited an NI point of 64.7° C. i.e. not lowered so much, a viscosity $\eta_{20}$ of 26.6 cp i.e. reduced, a Δε of 10.3 ($\epsilon_\parallel$ =15.1, $\epsilon_{195}$ =4.8) i.e. somewhat lowered and a Δn of 0.14 ($n_e$=1.63, $n_o$=1.49) i.e. unchanged. When this composition was filled in a TN cell of 9 μm thick same as the above, the threshold voltage lowered to 1.71 V and the saturation voltage lowered to 2.69 V.

EXAMPLE 7

(Use Example 2)

When trans-1-(3,3-difluoro-2-propenyl)-4-(4-cyanophenyl)cyclohexane obtained in Example 2 (15 parts by weight) was added to the liquid crystal composition A shown in Example 2 (85 parts by weight), the resulting liquid crystal composition exhibited an NI point of 55.6° C. a $\eta_{20}$ of 30.0 cp, a Δε of 10.0 ($\epsilon_\parallel$ =15.0, $\epsilon_\perp$=5.0) and a Δn of 0.13 ($n_e$=1.62, $n_o$=1.49). When the liquid crystal composition was filled in a TN cell of 9 μm thick same as the above, the threshold voltage lowered to 1.53 V and the saturation voltage lowered to 2.41 V.

EXAMPLE 8

(Use Example 3)

When trans-1-(4,4-difluoro-2-butenyl)-4-(4-cyanophenyl)cyclohexane obtained in Example 3 (15 parts by weight) was added to the liquid crystal composition A in Use example 1 (85 parts by weight), the resulting liquid crystal composition exhibited an NI point of 66.6° C., a $\eta_{20}$ of 23.9 i.e. lowered, a Δε of 10.7 ($\epsilon_\parallel$ =1.56, $\epsilon_\perp$=4.9) and a Δn of 0.13 ($n_e$=1.62, $n_o$=1.49). When this liquid crystal composition was filled in a TN cell of 9 μm thick same as the above, the threshold voltage lowered to 1.69 V and the saturation voltage lowered to 2.74 V.

As described above, when the composition of the formula (I) of the present invention is used as a component of liquid crystal compositions, a TN mode display element having a low driving voltage is obtained.

What we claim is:

1. A compound expressed by the formula

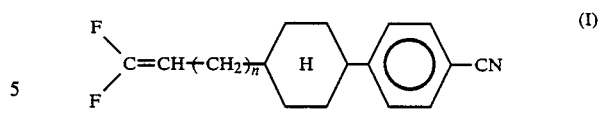

wherein n represents an integer of 0 to 20.

2. A compound according to claim 1 wherein said n represents an integer of 0 to 6.

3. A compound according to claim 1 wherein said n represents an integer of 0 to 4.

4. A liquid crystal composition comprising at least one member of the compound of the formula (I) as set forth in claim 1.